United States Patent [19]

Meguro et al.

[11] 4,349,547
[45] Sep. 14, 1982

[54] SUPPRESSING OBESITY AND OVER-SECRETION OF INSULIN WITH 2-(α-HYDROXY-M-TRIFLUOROMETHYL-BENZYL)AZETIDINE

[75] Inventors: Kanji Meguro, Hyogo; Hiroyuki Tawada, Osaka; Takao Matsuo, Kyoto, all of Japan

[73] Assignee: Takeda Chemical Industries, Ltd., Osaka, Japan

[21] Appl. No.: 178,951

[22] Filed: Aug. 18, 1980

[30] Foreign Application Priority Data

Aug. 24, 1979 [JP] Japan .................. 54/108329

[51] Int. Cl.³ .................. A61K 31/395; C07D 205/04
[52] U.S. Cl. .................. 424/244; 260/239 A
[58] Field of Search .................. 260/239 AR; 424/244

[56] References Cited

FOREIGN PATENT DOCUMENTS 1517934  7/1980  United Kingdom ........... 260/239 A

OTHER PUBLICATIONS

*Chemical Abstracts*, 89:117,867s, (1978), [German Ols 2,653,407, 6/1/78, Gold et al.].
*Chemical Abstracts*, 82:55495p, (1975), [Schade, D., et al., *Diabetes*, 1974, 23(8), 657–661].
March, J., *Advanced Organic Chemistry*, McGraw Hill, New York, 1968, p. 684.
Derwent Abstract 40579A/23 of German Pat. No. DT2653-407.

*Primary Examiner*—Richard A. Schwartz
*Attorney, Agent, or Firm*—Hubbell, Cohen, Stiefel & Gross

[57] ABSTRACT

2-(α-hydroxy-m-trifluoromethylbenzyl)azetidine and its physiologically acceptable acid addition salts have anti-obesity action as well as suppressive action against oversecretion of insulin.

4 Claims, No Drawings

SUPPRESSING OBESITY AND OVER-SECRETION OF INSULIN WITH 2-(α-HYDROXY-M-TRIFLUOROMETHYLBEN-ZYL)AZETIDINE

BACKGROUND OF THE INVENTION

1. Field of the Invention

This invention relates to a novel azetidine derivative having excellent pharmacological action.

2. Description of the Prior Art

German Patent Application Laid-Open No. 2653407 (DE-OS2653407) refers to 2-(α-hydroxybenzyl)azetidine and its acid addition salts as having antilipogenic and anorexigenic activity, as being suitable for treating fatty degeneration in mammals, and as reducing the conversion of carbohydrates to fats.

British Pat. No. 1,517,934 describes pharmaceutically active azacyclic compounds, including the compound

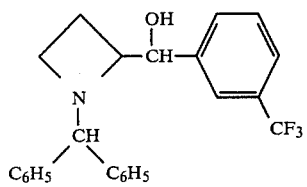

said compound being identified hereinafter as Compound VI. Such compounds are indicated as being suitable for the treatment of mammalian obesity.

SUMMARY OF THE INVENTION

The present inventors have succeeded in synthesizing 2-(α-hydroxy-m-trifluoromethylbenzyl)azetidine [hereinafter sometimes referred to as Compound (I) or briefly as (I)], which is represented by the formula

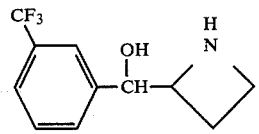

and have found that this compound and acid addition salts thereof have selectively marked antiobesity action.

Thus, this invention provides the novel azetidine derivative (I) and acid addition salts thereof, which compounds have an excellent pharmacological action. This invention also provides a pharmaceutical composition comprising one or more of Compound (I) and the salts thereof. The invention further provides an industrially feasible method for producing these compounds.

DESCRIPTION OF THE PREFERRED EMBODIMENTS

Compound (I), in theory, includes four different stereoisomers, and this invention encompasses all of the stereoisomers. The acid addition salt of Compound (I) is desirably a physiologically acceptable salt. Thus, such salts include the corresponding inorganic acid salts such as the hydrochloride, hydrobromide, sulfate, acid sulfate, phosphate, and the like, as well as such organic acid salts as the acetate, maleate, fumarate, succinate, tartrate, citrate, malate, etc.

Compound (I) of this invention can be readily synthesized, for example, by the process mentioned below:

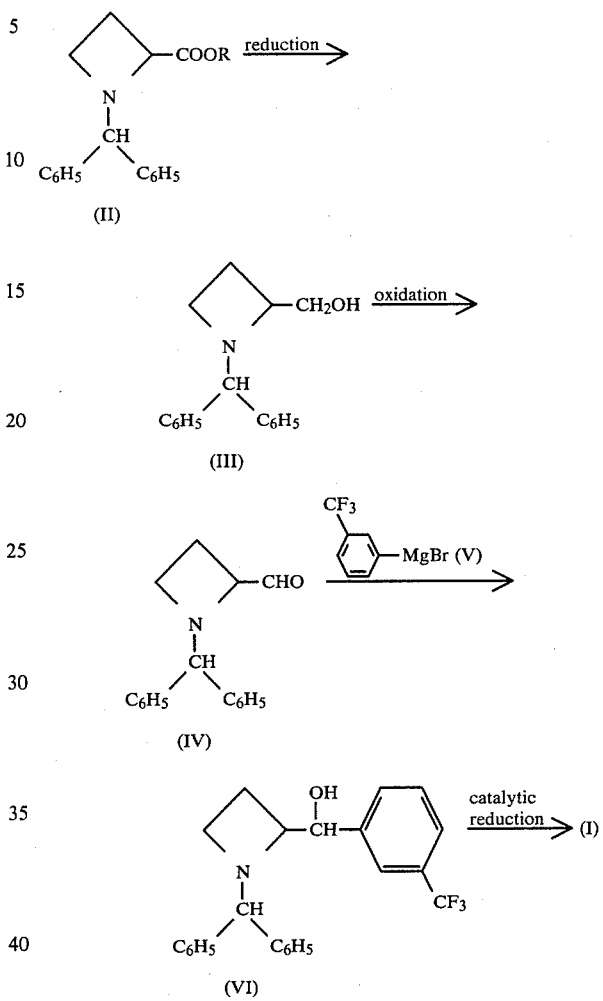

wherein R is lower alkyl or benzyl.

The lower alkyl group R is preferably of 1 to 4 carbon atoms, methyl and ethyl being especially desirable. The compound (II) wherein R is lower alkyl or benzyl can be synthesized by the process described in Journal of Heterocyclic Chemistry 8, 421 (1971) or a process analogous thereto. The reduction reaction of (II) to (III) can be carried out by a procedure known per se. For example, such a reaction can be conducted in anhydrous ethyl ether in the presence of lithium aluminum hydride at a temperature from room temperature to the boiling point of the solvent. The primary alcohol moiety of the resultant compound (III) is oxidized to a formyl group. This oxidation reaction can be effected advantageously with dimethyl sulfoxide. Oxidation with dimethyl sulfoxide and pyridine-sulfur trioxide complex is particularly desirable in that it does not involve any extensive side reaction. The oxidation reaction is usually carried out in dimethyl sulfoxide as the solvent at a temperature of about 0° to 40° C., using 1 to 5 equivalents and preferably 2 to 4 equivalents of the pyridine-sulfur trioxide complex.

The reaction of (IV) with (V) is usually carried out by the standard procedure which is used in the Grignard reaction, preferably in anhydrous ethyl ether, anhydrous benzene or a solvent mixture thereof, at a temperature from room temperature to the reflux temperature of the solvent. The compound (VI) produced by this reaction is a mixture of erythro- and threo-forms.

Either the isomeric mixture or each isomer as separated is subjected to the subsequent catalytic reduction step. Compound (VI), which is a known compound, can also be synthesized by the method described in British Patent No. 1517934 [corresponding to Japanese Patent Application Laid-Open No. 125273/51]. The catalytic reduction of (VI) is carried out by a process known per se, and it is particularly desirable to use palladium carbon or palladium black as a catalyst. When the product (I) is a mixture of erythro- and threo-forms, each of them may be separated and used as an antiobesity agent, or such isomeric mixture may be used as is. Separation of the erythro- and threo-forms of (VI) and of (I) can be accomplished by a routine method, e.g., recrystallization or chromatography. The erythro- and threo-forms of (I) can be further resolved, if desired, into their optically active forms and such optically active compounds can be used for the purposes of this invention.

Compound (I) of this invention has a specific activity to suppress the biosynthesis of fat from carbohydrate in addition to anorectic activity in animals, especially in mammals (e.g., mouse, rat, guinea pig, rabbit, cat, dog and man), being thereby capable of removing the excess body fat and reducing the body weight of such animals. Therefore, Compound (I) is of value as an antiobesity agent for mammals, i.e., an agent for the prophylaxis and/or treatment of obesity. Furthermore, Compound (I) has an action to suppress over-secretion of insulin in mammals and is suitable for the treatment of hyperinsulinemia, which is closely related with obesity. Compound (I) has low toxicity, good absorbability on oral administration, and high stability. Therefore, for medicinal uses such as those mentioned above, Compound (I) can be safely administered either as is or as formulated with an appropriate pharmaceutically acceptable carrier, vehicle or diluent. Thus, in the form of powders, granules, tablets, capsules, injections, etc., it can be administered orally or parenterally. The dosage will depend on the particular animal species, condition, age, body weight and administration route. When the compound is administered to an adult human being as an antiobesity agent, for instance, a daily dose of about 0.1 to 60 mg/kg, preferably about 1 to 20 mg/kg, may be taken, preferably in equally divided portions around meal times.

Although German Patent Application Laid-Open No. 2653407 (DE-OS2653407) refers to 2-(α-hydroxybenzyl)azetidine [hereinafter referred to briefly as (VII)] and its antiobesity action, it does not suggest any compound having the trifluoromethyl group as a substituent on the benzene ring. The Compound (I) of this invention exhibits very potent and long lasting antiobesity action, surpassing the action of (VII), by virtue of having a particular substituent, trifluoromethyl, in a particular position, i.e., the meta-position of the benzene ring.

The results of pharmacological tests which demonstrate the remarkable utility of Compound (I) of this invention are described below.

(a) Anorectic effect in mice

ICR mice, male and aged seven weeks (in groups of six individuals), which had been acclimatized to 6-hour/day feeding (CE-2 powder, commercial product of Clea Japan Ltd., Tokyo, Japan) for seven days were administered a dosage, by oral gavage, with a solution of 50 mg/kg of each test compound in 5% gum arabic at 0.5 hour before feeding on the eighth day, and the food intakes were compared with those of control mice given 5% gum arabic only. The results are set forth in Table 1. Each figure in the table is the percent food intake, with the corresponding figure for the control being 100.

TABLE 1

| Compound | Food intake (%) | | |
|---|---|---|---|
| | 0.5 hour after administration | 1 hour after administration | 2 hours after administration |
| Erythro-(I) hydrochloride | 44.0*** | 50.6*** | 67.0** |
| Threo-(I) hydrochloride | 55.0*** | 72.0** | 84.8 |
| Threo-(VII) hydrochloride (control compound) | 70.0* | 89.3 | 98.3 |

***P < 0.001,
**P < 0.01,
*P < 0.02

(b) Anorectic effect in rats

Sprague-Dawley (SD) rats, male and aged seven weeks, fasted for 24 hours (in groups of six individuals) were dosed, by oral gavage, with a solution of each test compound in 5% gum arabic, and feeding (CE-2 powder) was started at 0.5 hour after administration. The dose ($ED_{50}$) which caused a 50% inhibition of food intake as compared with the control dosed with 5% gum arabic was determined. The results are set forth in Table 2.

TABLE 2

| Compound | $ED_{50}$ (mg/kg) | | |
|---|---|---|---|
| | 0.5 hour after administration | 1 hour after administration | 2 hours after administration |
| Erythro-(I) hydrochloride | 20 | 20 | 25 |
| Erythro-(VII) hydrochloride (control compound) | 35 | 50 | 300 |

(c) Suppression of biosynthesis of fatty acid

Male SD rats fasted for 24 hours, were orally dosed with erythro-(I) hydrochloride and after a lapse of 30 minutes, glucose-U-$^{14}$C (140 μCi/2 g/kg) was orally administered. The animals were sacrificed after 60 minutes and the amounts of incorporation of glucose-U-$^{14}$C into the liver and the epididymal adipose tissue lipids were determined to calculate the dose ($ED_{50}$) which caused a 50% inhibition of glucose-U-$^{14}$C incorporation, as compared to control rats, which had fasted, had not been so dosed, and had been orally administered with glucose-U-$^{14}$C (140μCi/2 g/kg). The results were as follows:

Liver: $ED_{50}$=20 mg/kg.
Epididymal adipose tissue: $ED_{50}$=20 mg/kg.

(d) Suppression of insulin secretion

Fatty rats, female and aged 14 weeks, were used after fasting for 24 hours. The rats (in groups of five individuals) were orally dosed with a solution of 50 mg/kg of erythro-(I) hydrochloride in 5% gum arabic and, after 30 minutes, glucose (3 g/kg) was orally administered. At 30, 60 and 120 minutes after glucose loading, blood was withdrawn. The plasma samples were assayed for insulin and the insulin area was calculated. The results are given in Table 3.

TABLE 3

| Compound | Insulin area ($\mu$U/ml.hr) |
|---|---|
| Control | 739 |
| Erythro-(I) hydrochloride | 51* |

*$P < 0.01$ (e) Estimation of $LD_{50}$ in mice

ICR mice, male and aged nine weeks, were used without fasting. The mice (in groups of six individuals) were orally dosed with a solution of erythro-(I) hydrochloride (333, 500 and 750 mg/kg) or erythro-(VIII) hydrochloride (750, 1100 and 1700 mg/kg) in 5% gum arabic and kept for seven days. $LD_{50}$ was calculated using the Probit analysis. The results are shown in Table 4.

TABLE 4

| Compound | $LD_{50}$ (mg/kg) |
|---|---|
| Erythro-(I) hydrochloride | 499 |
| Erythro-(VII) hydrochloride | 902 |

The following examples are given by way of further illustration, and not by way of limitation.

EXAMPLE 1

(1) A solution of 5 g of benzyl 1-benzhydryl azetidine-2-carboxylate in 20 ml of anhydrous ethyl ether was added dropwise with stirring to a mixture of 0.53 g of lithium aluminum hydride and 20 ml of anhydrous ethyl ether. The mixture was stirred at room temperature for 30 minutes, and then 3.5 ml of water was added dropwise thereto under ice-cooling. The resulting precipitate was filtered off, and the filtrate was dried over anhydrous magnesium sulfate. After concentration, 20% ethanolic HCl was added thereto, whereupon crystals of 1-benzhydrylazetidine-2-methanol hydrochloride were obtained. Recrystallization from ethanol gave colorless prisms melting at 171°–172° C.

Elemental analysis, for $C_{17}H_{19}NO.HCl$: Calcd.: C, 70.46; H, 6.96; N, 4.83. Found: C, 70.31; H, 6.77; N, 4.80.

The above procedure was repeated, except that the benzyl ester was replaced with the methyl ester. The procedure provided 1-benzhydrylazetidine-2-methanol hydrochloride.

(2) To a stirred mixture of 9.0 g of 1-benzhydrylazetidine-2-methanol hydrochloride, 26.1 ml of triethylamine and 60 ml of dimethylsulfoxide were added dropwise a solution of 14.9 g pyridine-sulfur trioxide complex in 60 ml of dimethylsulfoxide. The mixture was stirred at room temperature for 30 minutes, after which it was poured into ice water and extracted with ethyl acetate. The extract was washed with water and dried over anhydrous magnesium sulfate, followed by removal of the solvent by distillation. The residue was recrystallized from n-hexane to yield 1-benzhydrylazetidine-2-carbaldehyde as colorless crystals melting at 88°–89° C.

Elemental analysis, for $C_{17}H_{17}NO$: Calcd.; C, 81.24; H, 6.82; N, 5.57. Found: C, 81.01; H, 6.84; N, 5.46.

(3) To a mixture of 0.42 g of magnesium turnings, 15 ml of anhydrous ethyl ether and small pieces of iodine there were added dropwise under mild reflux a solution of 3.93 g of m-bromobenzotrifluoride in 5 ml of ethyl ether to thereby prepare an ethyl ether solution of m-trifluoromethylphenylmagnesium bromide. To this solution was added dropwise a solution of 4.0 g of 1-benzhydrylazetidine-2-carbaldehyde in a mixture of 10 ml of anhydrous benzene and 10 ml of anhydrous ethyl ether. The whole mixture was stirred at room temperature for one hour and a solution of 2.5 g of ammonium chloride in 20 ml of water was added dropwise thereto. The organic layer was separated, and the aqueous layer was further extracted with ethyl ether. The combined organic layer was washed with water and dried over anhydrous magnesium sulfate. The solvent was then distilled off and n-hexane was added to the residue, whereupon crystals of erythro-1-benzhydryl-2-($\alpha$-hydroxy-m-trifluoromethylbenzyl)azetidine were obtained. The mother liquor was chromtographed on 60 g of silica gel and elution was carried out with n-hexane-ethyl ether (85:15), whereby an additional crop of erythro-compound was obtained. The two crops of crystals were combined and recrystallized from ethanol to yield colorless needles melting at 141°–142° C.

Elemental analysis, for $C_{24}H_{22}F_3NO$: Calcd.: C, 72.53; H, 5.58; N, 3.52. Found: C, 72.60; H, 5.54; N, 3.49.

When the above mentioned column was eluted with n-hexane-ethyl ether (7:3), there was obtained threo-1-benzhydryl-2-($\alpha$-hydroxy-m-trifluoromethylbenzyl)azetidine as an oil.

Elemental analysis, for $C_{24}H_{22}F_3NO$: Calcd.: C, 72.53; H, 5.58; N, 3.52. Found: C, 71.98; H, 5.61; N, 3.35.

(4) Four grams of erythro-1-benzhydryl-2-($\alpha$-hydroxy-m-trifluoromethylbenzyl)azetidine were catalytically hydrogenated in a solvent mixture of ethanol (80 ml) and 1 N-HCl (10 ml) in the presence of 10% palladium carbon as the catalyst at atmospheric temperature and pressure. The catalyst was filtered off and the solvent was distilled off, leaving crystals of erythro-2-($\alpha$-hydroxy-m-trifluoromethylbenzyl)azetidine hydrochloride. Recrystallization from acetonitrile gave colorless plates melting at 171°–172° C.

Elemental analysis, for $C_{11}H_{12}F_3NO.HCl$ Calcd.: C, 49.36; H, 4.90; N, 5.23. Found: C, 49.20; H, 4.64; N, 5.14.

(5) Threo-1-benzhydryl-2-($\alpha$-hydroxy-m-trifluoromethylbenzyl)azetidine was catalytically hydrogenated in the same manner as described in (4) above to thereby yield crystals of threo-2-($\alpha$-hydroxy-,-trifluoromethylbenzyl)azetidine hydrochloride. Recrystallization from isopropyl alcohol gave colorless needles melting at 176°–177° C.

Elemental analysis, for $C_{11}H_{12}F_3NO.HCl$: Calcd.: C, 49.36; H, 4.90; N, 5.23. Found: C, 49.10; H, 4.87; N, 5.11.

EXAMPLE 2

To use the Compound (I) of this invention as an antiobesity agent, for instance, the following formulations can be employed.

A. Tablets (1) Erythro-2-($\alpha$-hydroxy-m-trifluoromethyl-

| | | |
|---|---|---|
| | benezyl)azetidine hydrochloride | 10 g |
| (2) | Lactose | 90 g |
| (3) | Corn starch | 29 g |
| (4) | Magnesium stearate | 1 g |
| | (1000 tablets) | 130 g |

Components (1) and (2) were mixed with a 17 g portion of corn starch (3) and the mixture was granulated with a paste prepared from a 7 g portion of corn starch. To the granules were added the remaining 5 grams of corn starch (3) and component (4). The mixture was molded into 1000 tablets with a compression molding machine. Each of the tablets was 7 mm in diameter and contained 10 mg of component (1).

B. Capsules

| | | |
|---|---|---|
| (1) | Threo-2-(α-hydroxy-m-trifluoromethyl-benzyl)azetidine hydrochloride | 10 g |
| (2) | Lactose | 135 g |
| (3) | Finely divided cellulose powder | 70 g |
| (4) | Magnesium stearate | 5 g |
| | (1000 capsules) | 220 g |

All of the above components were mixed together and the Pharmacopoeia, 9th Ed.) to prepare an encapsulated product. Each capsule contained 10 mg of component (1).

C. Injection

| | | |
|---|---|---|
| (1) | Erythro-2-(α-hydroxy-m-trifluoromethyl-benzyl)azetidine hydrochloride | 1 g |
| (2) | Sodium chloride | 9 g |

The above components were dissolved in 1000 ml of distilled water and the solution was distributed into 1000 brown-colored ampules. The ampules were sealed after $N_2$ gas purging. The entire process was aseptically carried out.

Variations can, of course, be made without departing from the spirit of our invention.

What is claimed is:

1. A method for producing antiobesity action in a mammal, which comprises administering to the mammal an effective amount of 2-(α-hydroxy-m-trifluoromethylbenzyl)azetidine or a physiologically acceptable acid addition salt thereof.

2. A method of producing suppressive action against over-secretion of insulin in a mammal, which comprises administering to the mammal an effective amount of 2-(α-hydroxy-m-trifluoromethylbenzyl)azetidine or a physiologically acceptable acid addition salt thereof.

3. An antiobesity composition comprising 2-(α-hydroxy-m-trifluoromethylbenzyl)azetidine or a physiologically acceptable acid addition salt thereof, in an amount capable of producing an antiobesity action in a mammal, together with a pharmaceutically acceptable carrier, vehicle or diluent therefor.

4. An insulin suppressive composition comprising 2-(α-hydroxy-m-trifluoromethylbenzyl)azetidine or a physiologically acceptable acid addition salt thereof, in an amount capable of producing suppressive action against over-secretion of insulin in a mammal, together with a pharmaceutically acceptable carrier, vehicle or diluent therefor.

* * * * *